US011291999B2

(12) United States Patent
Yao et al.

(10) Patent No.: US 11,291,999 B2
(45) Date of Patent: Apr. 5, 2022

(54) PHOTOCLEAVAGE METHOD AND APPARATUS TO CLEAN FLUIDIC DEVICES

(71) Applicant: BioNano Genomics, Inc., San Diego, CA (US)

(72) Inventors: David Xian Wei Yao, San Diego, CA (US); William K. Ridgeway, San Diego, CA (US)

(73) Assignee: Bionano Genomics, Inc., San Diego, CA (US)

( * ) Notice: Subject to any disclaimer, the term of this patent is extended or adjusted under 35 U.S.C. 154(b) by 215 days.

(21) Appl. No.: 15/507,416

(22) PCT Filed: Aug. 31, 2015

(86) PCT No.: PCT/US2015/047688
§ 371 (c)(1),
(2) Date: Feb. 28, 2017

(87) PCT Pub. No.: WO2016/036647
PCT Pub. Date: Mar. 10, 2016

(65) Prior Publication Data
US 2017/0282181 A1 Oct. 5, 2017

Related U.S. Application Data

(60) Provisional application No. 62/044,823, filed on Sep. 2, 2014.

(51) Int. Cl.
B01L 3/00 (2006.01)
B08B 7/00 (2006.01)
C12Q 1/68 (2018.01)

(52) U.S. Cl.
CPC ......... B01L 3/502761 (2013.01); B01L 13/00 (2019.08); B08B 7/00 (2013.01);
(Continued)

(58) Field of Classification Search
CPC .................... B01L 3/502761; B01L 13/00
See application file for complete search history.

(56) References Cited

U.S. PATENT DOCUMENTS

2002/0072243 A1* 6/2002 Craighead ............... H01L 21/00
438/745
2007/0211985 A1* 9/2007 Duer .................... G01N 21/553
385/12
(Continued)

FOREIGN PATENT DOCUMENTS

JP 2011-525111 A 9/2011
WO WO 2009/155181 A1 12/2009

OTHER PUBLICATIONS

International Search Report and Written Opinion dated Nov. 26, 2015 in International Application No. PCT/US15/047688.
(Continued)

Primary Examiner — Lyle Alexander
Assistant Examiner — Dwan A Gerido
(74) Attorney, Agent, or Firm — Sheppard, Mullin, Richter & Hampton LLP

(57) ABSTRACT

A method and system for improving throughput of a fluidic system such as a biopolymer analysis system by cleaning accumulated or clogging biopolymer from the fluidic system is disclosed. The method and system utilize a light energy source to photocleave the biopolymer molecules that may accumulate or aggregate in the fluidic system or clog a passageway. The accumulated biopolymer may be exposed to a light energy source for a sufficient period of time such that the biopolymer molecule is dosed with sufficient energy to photocleave the biopolymer molecules, thereby restoring the efficiency of and flow through the system.

16 Claims, 5 Drawing Sheets

US 11,291,999 B2

Page 2

(52) U.S. Cl.
CPC ........ *C12Q 1/68* (2013.01); *B01L 2200/0663* (2013.01); *B01L 2300/0816* (2013.01); *B01L 2300/0864* (2013.01); *B01L 2300/0896* (2013.01); *B01L 2400/0406* (2013.01); *B01L 2400/0421* (2013.01); *B01L 2400/0487* (2013.01); *B01L 2400/086* (2013.01)

(56) References Cited

U.S. PATENT DOCUMENTS

2008/0274905 A1* 11/2008 Greene .............. G01N 21/6428
506/4
2009/0230044 A1* 9/2009 Bek .......................... B08B 3/12
210/198.1
2009/0312188 A1* 12/2009 Duer ................ B01L 3/502715
506/6

OTHER PUBLICATIONS

Office Action dated May 21, 2019 for European Patent Application No. 15763711.7.
Office Action dated Sep. 3, 2019 for Japanese Patent Application No. 2017-512288.
Office Action dated Sep. 9, 2019 for Chinese Patent Application No. 201580055371.2.
Office Action dated Feb. 24, 2021 in European Patent Application No. 15763711.7.
Notice of Allowance dated Aug. 11, 2020 in Japanese Patent Application No. 2017-512288.
Notice of Allowance dated Dec. 3, 2020 in Chinese Patent Application No. 201580055371.2.
Office Action dated Jun. 30, 2020 in Chinese Patent Application No. 201580055371.2.

* cited by examiner

PHOTOCLEAVAGE METHOD AND APPARATUS TO CLEAN FLUIDIC DEVICES

CROSS-REFERENCE TO RELATED APPLICATIONS

This application is a U.S. national phase under 35 U.S.C. § 371 of International Application No. PCT/US2015/047688, entitled PHOTOCLEAVAGE METHOD AND APPARATUS TO CLEAN FLUIDIC DEVICES, filed on Aug. 31, 2015, and published on Mar. 10, 2016 as WO/2016/036647, which claims the benefit of U.S. Provisional Application No. 62/044,823 filed on Sep. 2, 2014, which is hereby incorporated by reference in its entirety.

BACKGROUND

Field

The present disclosure relates to the field of nanotechnology and, more specifically, to linearizing molecules in nanofluidic and microfluidic channels.

Description of the Related Art

Biopolymers, such as proteins, DNA, or RNA, are often in the form of semi-flexible entwined polymeric chains. These macromolecules are normally assumed to have a random coil configuration in free solution. For double stranded DNA (dsDNA) in biological solution, the persistence length (a parameter defining its rigidity) is typically about 50 nm. In order to achieve consistent and accurate characterization of DNA and other biopolymers, it is often desirable that the biopolymer be moved through a fluidic channel to facilitate analysis or use of the biopolymer. In some instances, the biopolymer is linearized in a channel; in others, the biopolymer is directed through a fluidic flow path for other purposes. Further, to facilitate characterization of macromolecules and biopolymers, such as DNA, sequences or features of the macromolecule may be marked, for example, with fluorescent labeling techniques. Linearized, labeled biopolymers can then be optically imaged to provide certain information. However, optical mapping techniques for biopolymers have been hindered by low information density for optical maps, and conventional techniques provide only low-throughput capabilities. Although systems and methods for linearization and optical mapping providing an accurate, high-throughput characterization of biopolymer molecules are becoming more common, these systems are often hindered by the reduced throughput over time due to clogging of fluidic passageways, for example entrances into nanochannel or microchannel regions of nanofluidic and/or microfluidic linearizing systems including microfabricated structures such as pillar arrays. This clogging may occur regardless of whether the system is heavily loaded with DNA chains or lightly loaded, though in lightly loaded systems, the clogging may occur at a slower rate. Thus, systems and methods for cleaning and unclogging fluidic systems that handle biopolymers are needed.

SUMMARY

The systems, methods, and devices of the invention each have several aspects, no single one of which is solely responsible for its desirable attributes. Without limiting the scope of this invention as expressed by the claims which follow, some features will now be discussed briefly. After considering this discussion, and particularly after reading the section entitled "Detailed Description," one will understand how the features of the various embodiments of this invention provide advantages that include improved cleaning and increased throughput.

One aspect of this disclosure provides a method for enhancing fluid flow. In one aspect, the method includes moving biopolymer molecules into contact with at least one fluidic channel in or on a device, whereby clogging occurs in the device due to coiling or aggregation of the biopolymer molecules or adsorption to or tangling around the channels or any other nano- or micro-patterned features inside the channel or fluidic device, and directing a light source at a region of the device in which said clogging has occurred in a manner effective to photocleave biopolymers that contribute to said clogging, thereby facilitating removal or reduction of said clogging. In some aspects, the method further includes applying a motive force to fluid in the region of the device in a manner effective to flush the photocleaved biopolymer molecules from the region of the device comprising said clogging. In some aspects, the motive force may comprise an electrostatic force, a pneumatic force, a capillary force, or any combination thereof. In some aspects, the directing a light source comprises directing a light source having a wavelength of one of about 473 nm or about 488 nm to excite YOYO-1 bound to DNA. In some aspects, the biopolymer molecules being moved and photocleaved may comprise DNA or RNA.

In some aspects, the method also includes labeling the biopolymer molecules with an indicator or photon absorber to facilitate photocleavage of the biopolymer molecules when exposed to the light source. In some aspects, the light source may be configured to generate light matched to the indicator or photon absorber used to label the biopolymer molecules so as to maximize photocleavage of the biopolymer molecules when exposed to the light. In some aspects, the indicator used to label the biopolymer molecules may comprise one of YO, YOYO-1, YOYO-3, TOTO, methylene blue, Cu or Rh, compounds useful for photodynamic therapy, or any other photon absorber capable of facilitating photocleavage of the biopolymer. Each indicator can be excited with a specific wavelength or a range of wavelengths to induce photocleavage in an efficient manner. In some aspects, the method may further comprise detecting a clogged or reduced flow condition. In some aspects, the detecting comprises identifying that a transport of the biopolymer molecules through the device falls below a threshold transport value. In some aspect, the detecting comprises direct imaging of at least one fluidic channel in or on the device to indicate clogging. In some aspects, the cleaning of the region of the device in which the clogging has occurred is implemented in an automatic fashion at one of a predetermined time or a predetermined transport threshold. In some aspects, the method may further include positioning the light source in a manner effective to minimize exposure of the device to the light source.

Another aspect disclosed is an apparatus for enhancing fluid flow. In some aspects, the apparatus may include a light source configured to generate light configured to photocleave biopolymer molecules and a controller configured to control a movement of the biopolymer molecules into contact with at least one fluidic channel in or on a device, whereby clogging occurs in the device due to coiling or aggregation of the biopolymer molecules or adsorption to or tangling around the channels or other nano- or micro-patterned features inside the channel or fluidic device, direct the light source at a region of a device in which a clog of biopolymer molecules has formed, and activate the light source to generate the light beam for an amount of time to facilitate a photocleaving of the biopolymer molecules forming said clog.

In some other aspects, the apparatus further comprises a motive force generator configured to generate a motive force, wherein the controller is configured to control a movement of the biopolymer molecules via the generated motive force and wherein the controller is further configured to apply the motive force to fluid in the region of the device in which said clog occurred in a manner effective to flush the photocleaved biopolymer molecules from the region. In some other aspects, the motive force of the apparatus comprises at least one of an electrostatic force, a pneumatic force, a capillary force, or any combination thereof. In some aspects, the motive force generator is configured to generate one of an electrostatic force, a pneumatic force, a capillary force, or any combination thereof. In some aspects, the light beam generated by the light source may have a wavelength of one of about 473 nm or 488 nm. In some other aspects, wherein the biopolymer molecules or the apparatus may comprise DNA or RNA.

In some other aspects, the apparatus may further comprise a biopolymer molecule labeling device configured to label the biopolymer molecules with an indicator or photon absorber to facilitate photocleavage of the biopolymer molecules when exposed to the light beam generated by the light source. In some aspects, the indicator used to label the biopolymer molecules comprises at least one of YO, TOTO, methylene blue, Cu or RH, compounds useful for photodynamic therapy, or any other suitable photon absorber. In some aspects, the apparatus may further comprise a detector configured to detect a clog or reduced flow condition through the at least one fluidic channel in or on the device. In some aspects, the detector may be further configured to identify that a transport of biopolymer molecules through the at least one fluidic channel in or on the device falls below a threshold transport value. In some aspects, the detector may be further configured to directly image the at least one fluidic channel in or on the device to indicate the clog.

In some other aspects, the controller is further configured to operate the light source and enhance fluid flow in at automatic fashion at one of a predetermined time or a predetermined transport threshold. In some other aspects, the apparatus further comprises an x, x-y, or x-y-z translation motor configured to position the light source in a manner effective to minimize exposure of the device to the light source and further configured to allow positioning of the light source at any location in relation to the device.

In another implementation, light is directed to the region of the fluidic structure for the purposes of photocleavage by bringing a light-source such as an LED into close proximity to the fluidic structure without use of lenses or other optical systems. Either the LED or the fluidic structure could be translated into position to accomplish this. The controller would coordinate movements, light intensity and duration of exposure. A mask in between the light and the fluidic structure can be used to minimize exposure to regions that should not be subject to photocleavage or degradation, such as the sample well containing molecules that have yet to be loaded into the interrogation region of the chip.

Another implementation is to include light emitting regions into the fluidic device to apply local excitation and photocleavage to a particular region of the fluidic device that is subject to blockage or clogging.

Another aspect includes an apparatus for characterizing a biopolymer molecule. The apparatus comprises a fluidic device comprising a detection region comprising at least one channel and the biopolymer molecule. The apparatus further comprises a motive force generator that moves biopolymer molecules into the detection region, where a clog of biopolymer molecules may occur in the fluidic device and hamper further flow of new biopolymer molecules to the detection region. The apparatus further comprises a detection system for determining a characteristic of the biopolymer molecules in the detection region and a light source set to deliver a light comprising a configuration for photocleaving the biopolymer molecules forming the clog. The apparatus further comprises a light delivery system to deliver the light to any region of the fluidic device and a positioning system to target the detection system to the detection region for characterization of the biopolymer molecules, and to target the light comprising the photocleaving configuration to a region of the device where the clog has formed. The apparatus also comprises a controller configured to activate the motive force generator to move the biopolymer molecules into the detection region, direct the detection system to the detection region, activate the detection system to determine the characteristics of the biopolymer molecules, direct the light source configured for photocleaving biopolymer molecules to the region where the clog has formed, activate the light source to generate a light for photocleaving biopolymer molecules forming the clog, and activate the motive force generator to flush out the photocleaved biopolymer molecules; wherein additional new biopolymer molecules flow into the detection region for characterization.

Another aspect may include a method for characterizing a biopolymer. The method may comprise moving biopolymer molecules into a detection region of a fluidic device, whereby clogging may occur in the device, hampering further flow of biopolymers to the detection region. The method may further comprise detecting a characteristic of the biopolymer molecules in the detection region. The method may further comprise directing a light source at a region of the device where the clog has formed and photocleaving the biopolymer molecules causing the clogging. Then, the method may comprise applying a motive force to flush the photocleaved biopolymer molecules and applying a motive force to flow additional biopolymer molecules for characterization.

Another aspect may include another method for characterizing a biopolymer. The method may comprise moving biopolymer molecules into a detection region of a fluidic device and detecting a characteristic of the biopolymer molecules in the detection region. The method may further comprise directing a light source at the detection region wherein the light source comprises a configuration for photocleaving biopolymer molecules. The method further comprises photocleaving biopolymer molecules which have been characterized and flushing photocleaved molecules, allowing entry of new molecules for characterization.

Another aspect may include a system for characterizing a biopolymer. The system may comprise a fluidic device comprising a detection region comprising at least one channel, and further comprising the biopolymer and a detection system for determining a characteristic of the biopolymer molecule in the detection region. The system may further comprise a photo cleaving system comprising a light source set to deliver a light comprising a configuration for photocleaving biopolymer molecules that have already been interrogated or were not interrogated and do not need to be, for loading new molecules for characterization.

DETAILED DESCRIPTION

Figure 1:
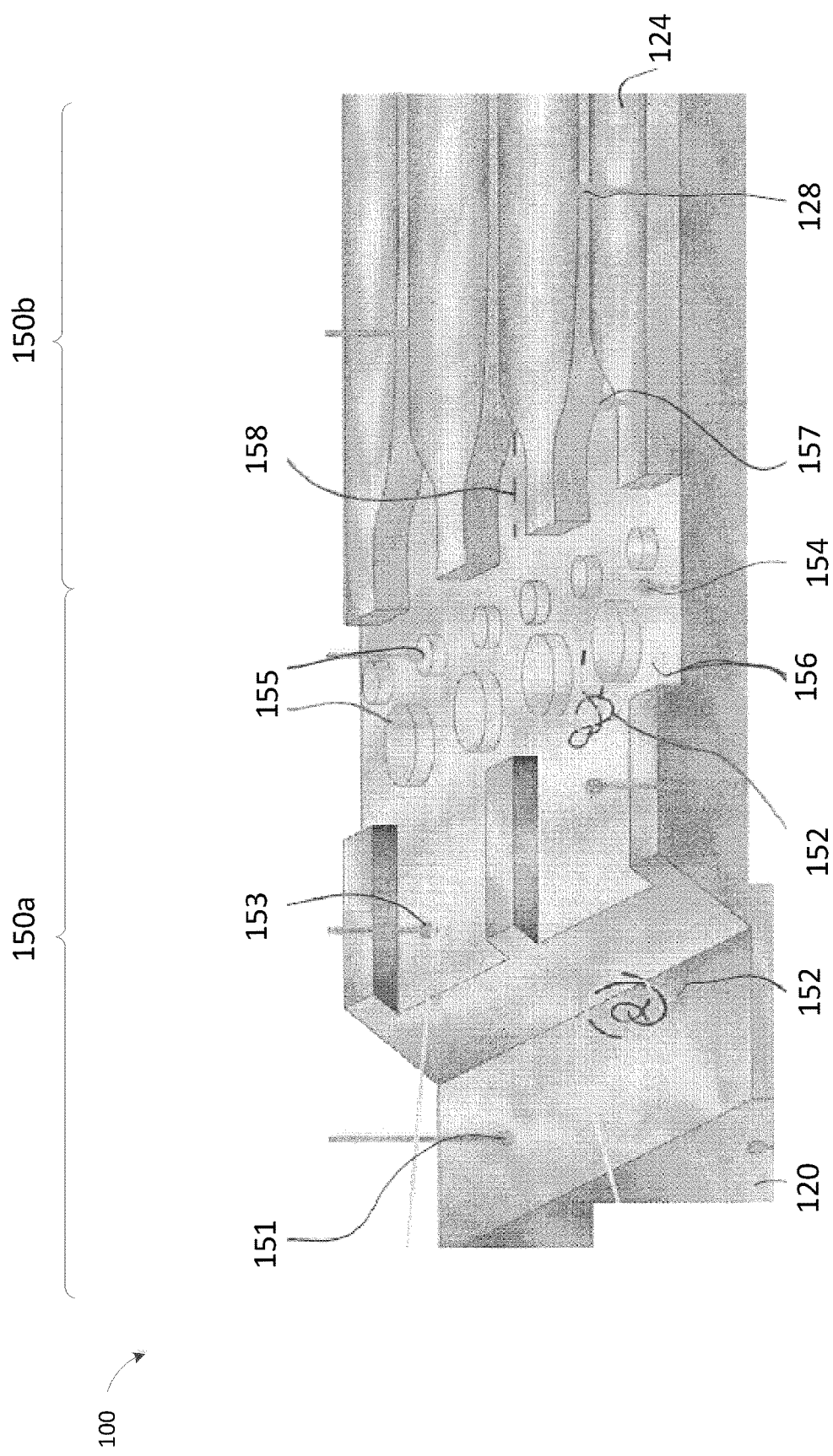
FIG. 1 is a schematic illustration of a non-limiting embodiment of a nanofluidic or microfluidic structure that may be used for biopolymer analysis.

In the description provided herein, reference is made to the accompanying drawings, which form a part hereof. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and made part of this disclosure.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any sub-combination. Further, reference to values stated in ranges includes each and every value within that range.

Unless defined otherwise, technical and scientific terms used herein have the same meaning as commonly understood by one of ordinary skill in the art to which this invention belongs.

As used herein, the term "channel" means a region defined by borders. Such borders may be physical, electrical, chemical, magnetic, and the like. The term "nanochannel" is used to clarify that certain channels are considered nanoscale in certain dimensions; similarly, the term "microchannel" is used to clarify that certain channels are considered microscale in certain dimensions. Also as used herein, nanofluidic may mean a fluid system having components whose dimensions are on the nanoscale, while microfluidic may mean a fluid system having components whose dimensions are on the microscale. As used herein, biopolymer analysis may refer to analysis of a macromolecule or biopolymer, such as DNA or RNA, using a nanoscale structure, such as a nanochannel, e.g., a nanofluidic system, and microanalysis may refer to analysis of a macromolecule or biopolymer, such as DNA or RNA, using a microscale structure, such as a microchannel, e.g., a microfluidic system. In some embodiments, biopolymer analysis may comprise biopolymer characterization, wherein a characteristic of the biopolymer molecule may include a physical dimension (i.e. length, width, etc.), a landmark periodicity, shape, enumerating molecules, size, density, electrical property, light scattering/refraction, etc.

As used herein, the term "nanochannel" may also refer to "microchannel." Thus, a device, system, or method that utilizes a nanochannel may be inferred to also apply to or be capable of utilizing a microchannel. Furthermore, any term utilizing the prefix "nano" may be replaced with the prefix "micro." For example, discussions of "nanochannels" or "nanofluidic" include "microchannels" and "microfluidic."

As used herein, the term "DNA" refers to DNA of any length (e.g., 0.1 Kb to 100 megabase). The DNA can be a highly pure preparation, crude, or semi crude material. The DNA can come from any biological source or can be synthetic.

As used herein, a "sample" may include any fluid containing a biopolymer that can be introduced into a microfluidic or nanofluidic device. The sample may include any fluid that contains a biopolymer of interest, for example purified and labeled DNA to be analyzed for optical genome mapping or sequencing. In some embodiments, the sample may be highly processed fluid that is applied to the nano- or microfluidic chip for analysis (i.e., an analyte). The sample can contain buffers and additives to modify the surface of the fluidic device to facilitate electrophoresis or prevent adsorption. In some embodiments, the sample can, for example, include one or more components of blood, serum, plasma, sputum, lavage fluid, cerebrospinal fluid, tissue, microorganisms, urine, semen, sweat, tears, saliva, and the like, including any fractions or processed portions thereof. Similarly, where a sample is taken from a biopsy, swab, smear, etc., the "sample" expressly encompasses a processed fraction or portion derived from the biopsy, swab, smear, etc.

Linearizing biopolymers may be beneficial in various biopolymer analysis systems. For example, linearization may be used in systems that image biopolymers, biopolymer optical mapping systems, sequencing systems, or in biopolymer transfection systems. Such linearization may be critical for studying, using, and/or analyzing the physical and biological properties of the biopolymer molecules. Some biopolymer analysis systems may use various methods or structures to linearize the biopolymers. In some embodiments, the biopolymer analysis system may include a fluidic device having a detection region, while in some embodiments, the biopolymer analysis system may include an apparatus having the fluidic device. The detection region may comprise at least one channel (e.g., a nanofluidic or microfluidic channel) through which the biopolymer flow. In some embodiments, the fluidic device may be a disposable, detachable unit (i.e., a chip as described below), a detachable, reusable unit, or a permanent or detachable part of the biopolymer analysis system or apparatus. For example, the fluidic device may be a Mapcard or similar unit. The detection region may comprise one or more fluidic channels (e.g., nano- or microfluidic channels). For example, some systems may utilize a tapered region to facilitate linearization and to introduce biopolymers into fluidic channels. Others may use a variety of obstacles or pillar regions or arrays through which the biopolymer molecules are fed via a motive force, the pillar regions or arrays causing the biopolymer molecules to straighten as they move through and around the pillars. Other systems may use confinement in nano- or microchannels, may feed the biopolymer molecules through nanoslits, nanopores, microslits, or micropores, or may insert the biopolymer molecules within reconfigurable tunable/elastomeric channels to linearize the biopolymers. Some may use open-topped channels on a surface of a substrate. Some systems may utilize other linearization methods or combinations of linearization methods and structures to linearize biopolymers. In the discussion below, various embodiments may be described. One of ordinary skill in the art would understand that these embodiments are a subset of the examples of fluidic systems in which biopolymers are directed and are not intended to be limiting except as specifically called out in claims.

For example, in a system for linearizing biopolymer molecules, nanochannels (or microchannels) can be used to straighten or transport the biopolymer molecules (e.g., DNA molecules) or maintain them in a linearized form to allow for imaging, mapping and/or sequencing of the biopolymer molecule. Such channels may be formed on or in nanofluidic (or microfluidic) chips or similar structures that may be easily replaceable or removable from a biopolymer analysis system or may be permanent fixtures of a biopolymer analysis system. In some embodiments, the nanofluidic or microfluidic structures may comprise one or more of the linearizing systems or methods discussed above. In other embodiments, the nanofluidic or microfluidic structures may comprise the linearizing systems or methods above and additional structures used by the biopolymer analysis system, e.g., a sample well or reservoir. The nanofluidic or microfluidic structures may comprise a plurality or an array of the nanochannels (or microchannels) therein that are used to translocate or straighten the biopolymers. High efficiency and high throughput imaging devices may have a large number of parallel arrays of nanochannels used for the linearization process, e.g., 10, 50, 100, 500, 1000, 5000 or more nanochannels in an array. In operation, the biopolymer analysis system may be repeatedly loaded with biopolymer molecules, and the biopolymer molecules may be directed to flow through the biopolymer analysis system (e.g., the fluidic device) under a motive force, e.g., an electrokinetic force, pneumatic force, a capillary force, or any combination thereof, to move the biopolymer molecules into the detection region. For example, flow of biopolymer molecules, through a biopolymer analysis imaging system may comprise flow through one or more linearization regions and the plurality of nanochannels may comprise an imaging region, where the biopolymer molecules, now having been linearized, may be effectively and efficiently imaged using imaging devices. In the biopolymer analysis system, a motive force, e.g., fluid pressure or an electric field, may be used to drive the biopolymer molecules through the system.

Further, the biopolymer analysis system or apparatus therein may comprise a detection system configured to determine a characteristic of the biopolymer molecules in the detection region of the fluidic device. In some embodiments, the detection system may comprise an optically-based device configured to use fluorescence to interrogate the biopolymer molecules. In some embodiments, the detection system may be an electrochemical detection system configured to operate independently of or in conjunction with the optically-based detection system (for example, for defining stretched biopolymer molecules). In some embodiments, the optically-based device configured to use fluorescence to interrogate the biopolymer molecules may use a same light source used for interrogation for photocleaving purposes. For example, when being used for photocleaving as opposed to interrogation, the light source may be tuned up (as is the case with the blue laser, 473 or 488 nm, used for backbone DNA detection and photocleaving. In some embodiments, the amount of energy required for photocleaving may be 10 to 100 times greater than the energy required for imaging. However, one or more optical detection components used for biopolymer molecule imaging (e.g., the CCD or CMOS camera) may not be used for biopolymer photocleavage.

The biopolymer analysis system may further comprise a motive force generator and a detection system, the detection system configured to determine a characteristic of the biopolymer molecules in the detection region. The light source described above may be configured to deliver a light comprising a configuration for interrogating biopolymer molecules or photocleaving biopolymer molecules forming a clog in the fluidic device. In some embodiments, the light source may comprise one or more lasers with a specific or adjustable wavelength, an LED/OLED, an incandescent lamp, a mercury lamp, a UV lamp, an arc lamp, an argon lamp, or any other gas lamp (e.g., neon and krypton). The light source can be pulsating (i.e., turned on for a finite amount of time in bursts) or continuous, gated by physical shutters, filtered, amplified, dampened, polarized, or otherwise manipulated to generate a light used to interrogate biopolymer molecules at a variety of different wavelengths and intensities.

In some embodiments, the energy used for photocleavage may be destructive to multiple species of label. For example, labels that are red-shifted in emission, such as Cy3 or Atto 532, may be destroyed or damaged by a 488 nm light source used to photocleave biopolymer molecules labeled with YOYO-1. Thus, the use of photocleavage processes and energies may inhibit subsequent attempts to image such biopolymer molecules that have been photocleaved, and care must be used to ensure the photocleavage has minimal effects on non-targeted biopolymer molecules and labels. In some embodiments, matching of the light generated by the light source to the label to be photocleaved may reduce the destructive effects of the light on non-targeted species of label. Additionally, in an optical detection system using fluorescence, additional wavelengths may be used for target multiplexing (targets being landmarks within a molecule, i.e. a defined sequence in a DNA), or sample multiplexing (different samples labeled with different colors or color combinations).

In some embodiments, the optically-based detection system may further comprise mirrors, objectives, lenses, filters, shutters, fiber optic cable, or any combination thereof. The optically-based detection system may further comprise a focusing mechanism to ensure maximum photon delivery for photocleaving (where the light source of the detection system is used for photocleaving and interrogating) and to provide tight focus for maximum clarity when interrogating biopolymers.

In some embodiments, a light delivery system may be configured to deliver the light generated by the light source to any region of the fluidic device. The light delivery system may comprise an optical system, or close proximity based delivery system bypassing the optical system, or a combination of the two, wherein DNA detection and interrogation of biopolymer molecules may occur via the optical system and photocleaving may occur by direct irradiation while protecting biopolymer molecules outside the interrogation zone.

The biopolymer analysis system may further include a positioning system and a controller, wherein the positioning system may be configured to target the detection system to the detection region for characterization of biopolymer molecules and to target a photocleaving light to a region of the fluidic device where the clog has formed. In some embodiments, the positioning system may be capable of movement in one or more of the x-, y-, and z-directions. In some embodiments, the positioning system may include a lag-screw based motion system or a piezo or stick-slip motion system. In some embodiments, the positioning system may include an internal or external encoder or another feedback mechanism to achieve accurate positioning.

In some embodiments, a controller may be configured to activate the motive force generator to move biopolymer molecules into the detection region and to direct the detection system to the detection region. The controller may be further configured to activate the detection system to determine characteristics of the biopolymer molecules. When a clog has formed in the fluidic device, the controller may direct the light source configured for photocleaving biopolymer molecules to the region where the clog has formed and activate the light source to generate a light for photocleaving biopolymer molecules forming the clog. Thereafter, the controller may activate the motive force generator to flush out the photocleaved biopolymer molecules so that additional new molecules can flow into the detection region for characterization.

FIG. 1 depicts an embodiment of a nanofluidic or microfluidic structure 100 that may be used in a biopolymer fluidic system. The components of an embodiment of the nanofluidic or microfluidic structure 100 are depicted. The nanofluidic or microfluidic structure 100 is adjacent to a sample well 120 or other sample source, such as a larger fluidic channel. The sample well 120 may be filled with a liquid sample containing a biopolymer or macromolecule, for example DNA molecules 152. The fluid sample can also contain buffer for purposes of electrophoresis and surfactants and other additives for surface modification. The movement of DNA molecules 152 through the nanofluidic or microfluidic structure 100 is described herein as an example, and embodiments of the present disclosure are not limited thereto. While the biopolymers or macromolecules described herein are exemplified by DNA molecules 152, one of skill in the art will understand this is merely an example of a biopolymer and not limiting.

The nanofluidic or microfluidic structure 100 may be divided into various zones, such as a transition zone 150a and a nanochannel zone 150b. The transition zone 150a can include a lip region 151, one or more feeder channels 153, a pillar or deconvolution or linearizing region 154, and one or more relaxation channels 157. The lip region 151 is advantageously adjacent to a sample well 120 and may comprise a raised portion with respect to the sample well 120. The lip region 151 can be the first part of the nanofluidic or microfluidic structure 100 that the DNA molecule 152 encounters when being moved, translocated, or otherwise driven from the sample well 120 using, for example, electrophoresis. The lip region 151 provides a transition area for DNA molecules 152 leaving the sample well 120 and entering the subsequent regions of the nanofluidic or microfluidic structure 100. A coiled or entangled DNA molecule 152 is depicted in the lip region 151, having been driven from the sample well 120. The lip region 151 may have a depth of from about 0.1 microns to about 10 microns, as measured from a top surface of the well structure 124. The lip region may be from about 0.5 micron to about 1000 microns in length, wherein length is defined as being in the direction transversing the nanofluidic or microfluidic structure 100 from one sample well 120 to another. In some embodiments, the lip region is about 1.5 microns deep and about 15 microns in length. The dimensions provided herein are exemplary only, and the dimension may be construed to be any value within the listed ranges.

Adjacent to the lip region 151 are the one or more feeder channels 153. The feeder channels 153 funnel or direct the coiled or entangled DNA molecules 152 into a pillar region 154. The one or more feeder channels 153 run parallel to each other, and are wide channels, relative to the nanochannels 128. The feeder channels 153 may have a width of about 0.05 microns to about 25 microns, or any value therebetween, wherein width is understood to be in a direction perpendicular to length as described above. The feeder channels 153 may have a depth of from about 20 nm to about 1000 nm, or any value therebetween. In some embodiments, the feeder channel is about 50 nm in depth and about 1.5 microns wide.

In one embodiment, the feeder channels 153 may lead to the pillar region 154. The pillar region 154 includes a floor 156 which, in some embodiments, is contiguous with the bottom surface of the feeder channels 153. The pillar region 154 also includes one or more pillars 155. The pillars 155 may be silicon formations which are interspersed throughout the pillar region, with the pillars 155 extending from the floor 156 of the pillar region to a top portion which is raised above the floor 156. In some embodiments, the top portion of the pillar region is in the same plane as the top surface of the well structure 124, and may be in contact with the substrate (not shown). The pillars 155 may be of any shape, that is, the pillars may have a cross-sectional shape which is round, square, diamond, ovoid, rectangular, or any other desired shape. The pillars 155 may vary from one to another in size, shape, height, and distance from other pillars 155. The pillars 155 may be evenly spaced or unevenly spaced throughout the pillar region 154. In some embodiments, the pillar region 154 may include multiple zones (e.g., two or more zones) of pillars 155, wherein a first zone comprises pillars of one a first dimension, shape, and/or height, and a second zone of pillars comprises pillars 155 of a second dimension, shape, and/or height, different from the first dimension. In one embodiment, the pillars 155 vary from larger to smaller dimension as they are further removed from the feeder channels 153 and closer to the nanochannels 128.

The pillars 155 within the pillar region 154 are sized, shaped, and positioned to untangle, uncoil, or otherwise straighten tangled or coiled biopolymers or macromolecules. For example, the size of the pillars 155 and the spacing between the pillars 155 creates a tortuous flow path through which the coiled or tangled DNA molecule 152 cannot fit. Thus, as a motive force, such as an electrostatic field, is applied across the nanofluidic or microfluidic structure 100, the coiled or tangled DNA molecule 152 is mechanically forced to uncoil as the molecule interacts with the pillars 155. As shown, there may be more than one zone of pillars 155, and the pillars 155 of the different zones may have different properties. For example, in some embodiments, the spacing between the pillars 155 of the first zone may be larger than the spacing of the pillars 155 of the second zone. In this way, the first zone causes an initial partial untangling or uncoiling, before the molecules reach the second zone. In the second zone, the molecules are forced through narrower spaces, which can cause a further untangling or uncoiling of the molecules. The distance between pillars 155 can vary. For example, the distance between two pillars 155 can be about 25 nm, about 50 nm, about 100 nm, about 150 nm, about 200 nm, about 250 nm, about 300 nm, about 350 nm, about 400 nm, about 450 nm, about 500 nm, about 1000 nm, about 2000 nm, about 3000 nm, about 4000 nm, about 5000 nm, or a range between any two of these values. In some embodiments, the distance between pillars 155 is about 0.1 micron to about 2.5 microns.

The pillars 155 may have a height, that is, a distance from the floor 156 to their top surfaces of from about 20 nm to about 5000 nm, or any value therebetween. In some embodiments, the pillars 155 may have a width, diameter, or long dimension, depending on their shape, of from about 50 nm to about 10000 nm, or any value therebetween. In some embodiments, the pillars 155 have a height of about 50 nm and a width, diameter, or long dimension, of from about 200 nm to about 5000 nm. As shown, the pillars 155 of the different zones may be of different diameters, where the pillars 155 of the first zone may have a larger diameter than the pillars 155 of the second zone. Additionally, the density of the pillars 155 in the pillar region 154 may increase as pillar region 154 nears the nanochannel wells 128.

The pillar region 154 adjoins a plurality of relaxation channels 157. The relaxation channels 157 are channels that act as inlets to the plurality of nanochannels 128. In some embodiments, the relaxation channels 157 are funnel shaped channels. The relaxation channels 157 have a wider dimension at an end adjacent to the pillar region 154 and a narrower dimension at an end proximate to the nanochannels 128. The relaxation channels 157 receive uncoiled and untangled or partially uncoiled and untangled molecules and help to further linearize the molecules as the molecules enter the plurality of nanochannels 128. A linearized DNA molecule 158 is depicted entering one nanochannel 128 from the associated relaxation channel 157. The relaxation channels 157 may be from about 10 to about 5000 microns long, about 20 nm to 300 nm deep, and about 50-1000 nm wide. In some embodiments, the relaxation channels 157 may be about 80 microns long, 50 nm deep, and 300 nm wide, at their widest point.

The plurality of nanochannels 128 receive the linearized DNA molecules, and are sized such that only linearized molecules can fit into and can be transported or moved through the nanochannels 128. The nanochannels 128 may be from about 20 nm to about 300 nm wide, about 30 to about 300 nm deep, and from about 10 to about 10000 microns long. In some embodiments, the nanochannels are about 45 nm wide, about 45 nm deep, and about 350 microns long.

During use, it is possible for the nanochannel 128 to become clogged with the biopolymer molecule 152 that is being translocated through the nanochannel 128 (see clog 130). The clog may hamper further flow of new biopolymer molecules through the nanochannel 128 and/or the fluidic device. In other instances, the nanochannel 128 may be clogged where they meet with the relaxation channel 157 (see clog 132) or the relaxation channels 157 may become clogged or blocked by DNA molecules 112 that do not fully uncoil through the pillar region 154 or that re-coil once they pass through the pillar region 154 (see clog 134). Alternatively, the pillar region 154 may become clogged by DNA molecules 152 that do not properly uncoil or that wrap around one or more pillars 155 and accumulate (see clog 136). Additionally, a clog 138 may form where the sample well 120 meets the feeder channels 153.

In a more general sense, as applied to fluidic devices in general, DNA or other biopolymer may accumulate or clog in any region of fluid flow, but more usually in branch points, valves, transitions from larger to smaller channels, points where turbulent flow occurs, entrances to channels smaller than the dimension of coiled biopolymer, waste channels, flow passages of low velocity, regions where flow is stopped for a period of time, or areas where biopolymer may aggregate or precipitate or become adsorbed upon or entangled with any surface of the fluidic device including pillars, sidewalls of the nanochannels, or any other linearization structure.

Figure 2:
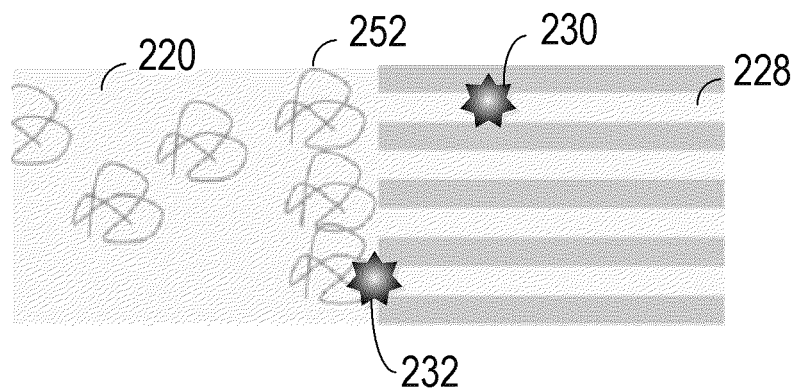
FIG. 2 depicts an alternate non-limiting embodiment of a nanofluidic or microfluidic structure that may be used for biopolymer analysis.

FIG. 2 depicts an alternate embodiment of a nanofluidic or microfluidic structure 200 that may be used for biopolymer analysis. The components of an embodiment of this nanofluidic or microfluidic structure 200 are depicted and may be similar to those described in relation to FIG. 1. The nanochannel 228 is shown adjacent to a sample well 220. In some embodiments, both the nanochannel 228 and the sample well 220 may be part of the nanofluidic or microfluidic structure 200. In other embodiments, only the nanochannels 228 may be part of the nanofluidic or microfluidic structure 200. The sample well 220 may be filled with a liquid sample containing a biopolymer or macromolecule, for example DNA molecule 252. The liquid sample can also contain buffer for purposes of electrophoresis and surfactants and other additives for surface modification. The movement of DNA molecules 252 through the nanochannel structure 200 is described herein as an example, and embodiments of the present disclosure are not limited thereto. While the biopolymer or macromolecule described herein are described as DNA molecules 252, one of skill in the art will understand this is merely an example of a biopolymer and is not limiting.

Coiled or entangled DNA molecule 252 is depicted in the sample well 220. Adjacent to the sample well 220 are the plurality of nanochannels 228. The plurality of nanochannels runs parallel to each other. The plurality of nanochannels 228 receive the linearized DNA molecules and may be sized such that only significantly linearized molecules can fit into and can be transported or moved through the nanochannels 228. The nanochannels 228 may advantageously be from about 20 nm to about 300 nm wide, about 30 to about 300 nm deep, and from about 10 to about 10000 microns long. In some embodiments, the nanochannels 228 are about 45 nm wide, about 45 nm deep, and about 350 microns long. As depicted, one or more DNA molecules 252 may be located in one of the one or more sample wells 220 and/or the plurality of nanochannels 228. In some embodiments, the DNA molecules 252 may be located in both a sample well 220 and a nanochannel 228 at the same time.

The size and the spacing of the nanochannels 228 may create a restrictive flow path through which the coiled or tangled DNA molecule 252 cannot fit. Thus, as the motive force, such as an electric field, is applied across the nanofluidic or microfluidic structure 200, the coiled or tangled DNA molecule 252 is mechanically forced to uncoil as the molecule interacts with the nanochannels 228 from the sample well 220.

During use, it is possible for the nanochannel 228 to become clogged with the biopolymer molecule 252 that is being translocated through the nanochannel 228 (see clog 230). Alternatively, the point where the sample well 220 and the nanochannels 228 meet may become clogged or blocked by coiled DNA molecules 228 that do not properly uncoil under the motive force as they should to move into the nanochannel 228 (see clog 232).

Figure 3:
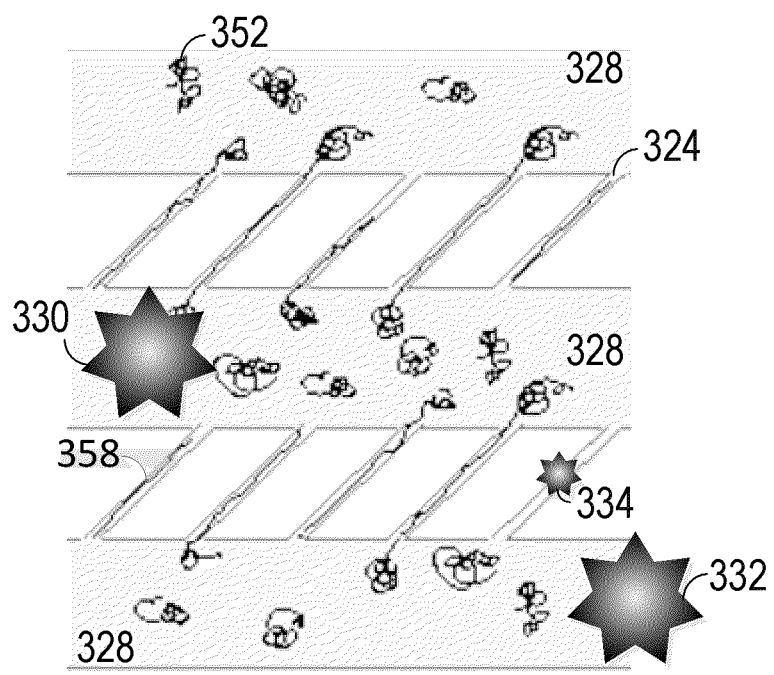
FIG. 3 depicts another non-limiting embodiment of a nanofluidic or microfluidic structure that may be used for biopolymer analysis.

FIG. 3 depicts another embodiment of a nanofluidic or microfluidic structure 300 that may be used for biopolymer analysis. The components of an embodiment of this nanofluidic or microfluidic structure 300 are depicted and may be similar to those described in relation to FIG. 1. In some embodiments, the nanofluidic or microfluidic structure 300 may comprise a nanochannel 328 and a sample well (not shown). In other embodiments, only the nanochannels 328 may be part of the nanofluidic or microfluidic structure 300.

The sample well may be filled with a liquid sample containing a biopolymer or macromolecule, for example DNA molecule 352. The liquid sample can also contain buffer for purposes of electrophoresis and surfactants and other additives for surface modification. The movement of DNA molecules 352 through the nanochannel structure 300 is described herein as an example, and embodiments of the present disclosure are not limited thereto. Nanoslits 324 may exist between each of the nanochannels 328. As depicted, the nanoslits 324 may run diagonally between two nanochannels 328. The nanoslits 324 may work to linearize the DNA molecules 352 when the nanochannels 328 are loaded with the DNA molecules 352 and the DNA molecules 352 pass through the nanoslits 324. As depicted, one or more DNA molecules 352 may be located in one of the one or more nanochannels 328 and/or one or more nanoslits 324. In some embodiments, the DNA molecules 352 may be located in both a sample well, a nanochannel 328, and a nanoslit 324. While the biopolymer or macromolecule described herein are described as DNA molecules 352, one of skill in the art will understand this is merely an example of a biopolymer and is not limiting.

A coiled or entangled DNA molecule 352 is depicted in the one or more nanochannels 328. The plurality of nanochannels runs parallel to each other. The nanochannels 328 may be from about 20 nm to about 300 nm wide, about 30 to about 300 nm deep, and from about 10 to about 10000 microns long and may receive linearized or coiled DNA molecules 352. In some embodiments, the nanochannels 328 are about 100 nm wide, about 100 nm deep, and about 350 microns long. In some embodiments, the nanoslits 324 are about 45 nm wide, about 45 nm deep, and about 45 microns long. In some embodiments, the DNA molecules 352 may be located in both a sample well and a nanochannel 328 at the same time. A linearized DNA molecule 358 is depicted flowing through one nanoslit 324.

The nanofluidic or microfluidic structure 300 may be used to translocate at least a portion of a biopolymer molecule from the sample wells through the nanochannel 328. However, during use, it is possible for the nanochannel 328 to become clogged with the DNA molecule 352 that is being translocated through the nanochannel 328 (see clog 330). Alternatively, the region where the sample wells and the nanochannel 328 meet may become clogged or blocked by coiled or accumulated DNA molecules 352 (see clog 332). Additionally, the nanoslits 324 may become clogged or blocked by DNA molecules 352 (see clog 334).

Once clogged, the efficiency of the linearization process using the clogged nanofluidic or microfluidic structures may decrease. Also, once clogged it can be difficult to introduce fresh biopolymer molecules into the nanofluidic or microfluidic device and manipulate them therein, seriously limiting throughput and utility. Clogging can further change the optimal electrical conditions required to manipulate biopolymer molecules in the nanofluidic or microfluidic structure, resulting in subpar throughput. Heterogeneous clogging throughout a plurality of nanochannels can give rise to heterogeneous response to electric fields from one portion of the microfluidic or nanofluidic device to the next. The rate of clogging can increase when existing biopolymer molecules are clogged inside the nanofluidic or microfluidic device, creating a snowball effect that accelerates clogging. Given the size of the nanochannels of the nanofluidic or microfluidic structure, clearing the channels through physical or similar means (e.g., cleaning solutions or physical cleaning devices) may be difficult and/or impractical.

Nanofluidic or microfluidic structures, including but not limited to those depicted in FIGS. 1-3 may initially achieve a high throughput when loading the biopolymer molecules into the nanochannel or microchannel region. As the linearization region and nanochannels are repeatedly used for linearizing more biopolymer molecules, the linearization region and nanochannels may become clogged with tangled or accumulated biopolymer molecules. Similarly, the nanochannels may become clogged by molecules that are not completely linearized when they enter into the nanochannels or when multiple molecules enter a nanochannel at one time. Such tangling and/or clogging can cause reduced throughput as the clogged portions inhibit the ability for the DNA molecules to flow through the desired flow passages, such as nanochannels. For example, over time, when driving DNA through an array of nanochannels, more and more nanochannels will become clogged, so fewer channels can be used to provide information. The reduced number of DNA molecules traveling through the nanochannels results in reduced throughput or reduced information density in the array. Other fluidic devices can similarly become clogged with DNA or other biopolymers, reducing their utility in a related manner.

Accordingly, the clogged portion of the nanofluidic or microfluidic structure may need to be cleaned to restore the throughput of the chips or other structures. As an example, with reference to the structure of FIG. 1, one method for clearing out the pillar region and the nanochannels may comprise using a laser or other illumination source to chop the biopolymer molecules that are clogging portions of the nanofluidic or microfluidic structure into fine pieces, after which those pieces of the chopped biopolymer molecules may be flushed from the nanofluidic or microfluidic structure via an appropriate motive force, such as by electrophoretic force or fluid pressure differential. In some embodiments, the biopolymer molecules may be "YoYo-1" stained or labeled biopolymer molecules. In some other embodiments, the biopolymer molecules being chopped/photocleaved may be stained or labeled with another indicator or exposed to another compound (i.e., YO, TOTO, methylene blue, Cu or Rh, compounds for photodynamic therapy, etc.) that absorb photons to facilitate or aid photocleavage of the biopolymer molecules when exposed to an illumination source. Thus, photocleavage may be achieved with or without a stain, label, indicator, or other photon absorber. Alternate embodiments may utilize non-stained molecules. In some embodiments, the illumination source may be a laser, for example a 473 nm blue laser or a 488 nm laser, or a laser of any other wavelength. Other embodiments may utilize light energy sources of other wavelengths, e.g. UV light, and light energy from other sources, e.g. a light-emitting diode. Thus, laser or other light that matches or overlaps an absorption wavelength of a dye or other absorbing molecule on the biomolecule can be used to cleave a labeled polynucleotide or other biomolecule, and UV or other high-energy illumination sources can be used to cleave even unlabeled polynucleotide or other biomolecule.

By applying a dose of laser or other light energy to the nanofluidic or microfluidic structure at desired times or intervals, clogging biopolymer molecules or stained/labeled biopolymer molecules that can absorb or be cleaved by the light may be fragmented, and more easily flushed from the structure. In one embodiment, specific times in a repetitive fluidic process, such as interleaved loading and imaging cycles in an analysis device, may be defined as the times when clogging biopolymers should be removed. Alternatively, the amount of clogging can be at least partially ascertained by detecting reduction of throughput or channels containing biomolecule beyond a threshold amount. Alternatively, direct imaging of the chip can indicate clogging. Alternatively, cleaning can be initiated during times when the nanofluidic or microfluidic structures are not currently being used for linearization.

For example, with reference to the structure of FIG. 1, the device may detect or measure the throughput or loading density of the downstream nanochannels when the pillar regions of the nanofluidic or microfluidic structure are new and entirely unclogged. The system may be configured to detect clogging in the nanofluidic or microfluidic structure. The clog may be detected by identifying a reduced throughput or loading density in the nanochannels. Some embodiments may comprise additional detection methods to determine where the clog is located within a nanofluidic or microfluidic structure. Once the specific location of the clog is determined, the system may focus the illumination source at that location to focus the dosing energy only where needed and not wasting energy by unnecessarily dosing portions of the biopolymer analysis system that are not clogged. Alternatively, the system may direct illumination energy effective to fragment clogging biopolymers at least into any or all regions of the fluidic device that are susceptible to clogging.

In one embodiment, an initial throughput or loading value in a new or unclogged fluidic device may be determined to be a baseline throughput of the nanofluidic or microfluidic structure and may be the basis for determining a threshold level at which point the nanofluidic or microfluidic structures are to be cleaned. In some embodiments, the threshold level may be set as 50% of throughput, such that when the throughput of the downstream nanochannels falls below 50%, the device cleans the pillar regions of the nanofluidic or microfluidic structures. In another embodiment, the threshold level may be set at 75% of throughput or 25% of throughput, or any value in between these values, or at any other desired threshold, dependent on the requirements for the nanochannel throughput and the ability to clean the pillar region with an appropriate dose of biopolymer-cleaving energy (i.e., the device may have an automated ability to apply the photo-energy dose more or less frequently). Alternatively, the nanofluidic or microfluidic structure may be dosed after every loading cycle to ensure the structure is as clear as possible. In any of the embodiments of cleaning described herein, the cleaning process may be implemented in an automatic fashion, including at a predetermined time or at a predetermined clogging, throughput, or loading value.

Figure 4:
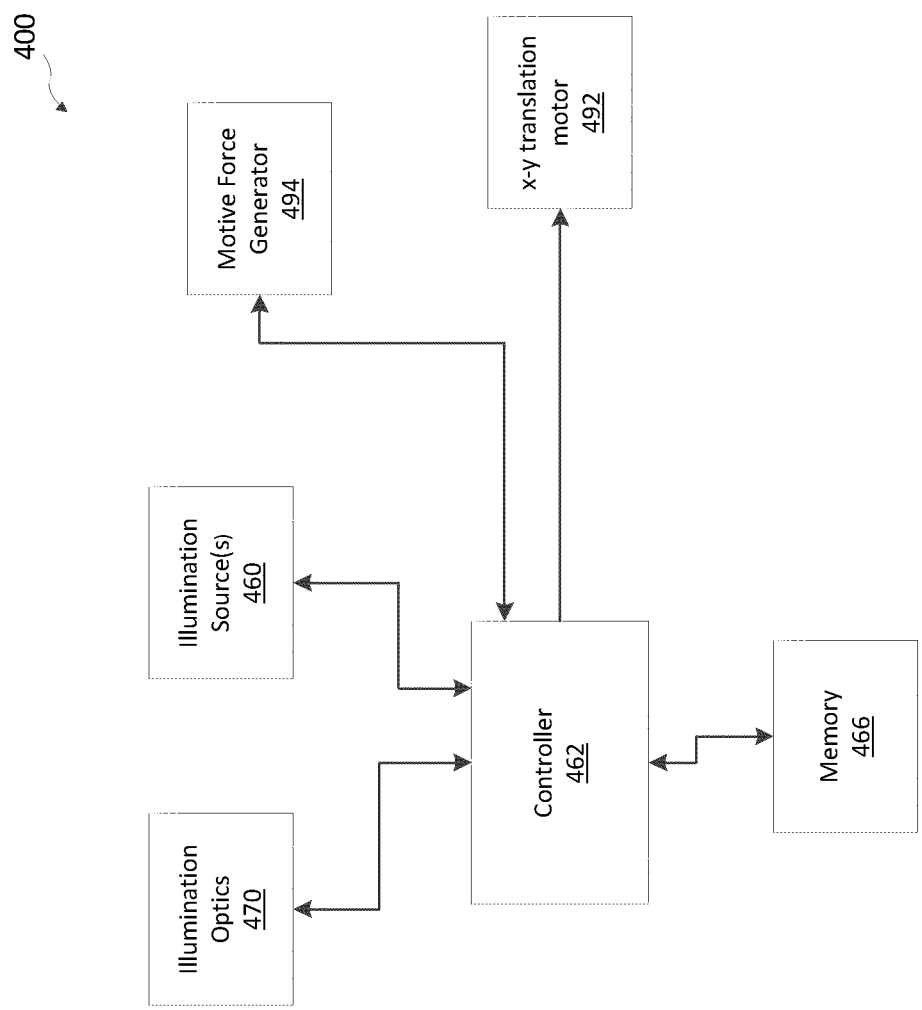
FIG. 4 is a block diagram of a non-limiting embodiment of a control system for a system for biopolymer analysis.
Figure 5:
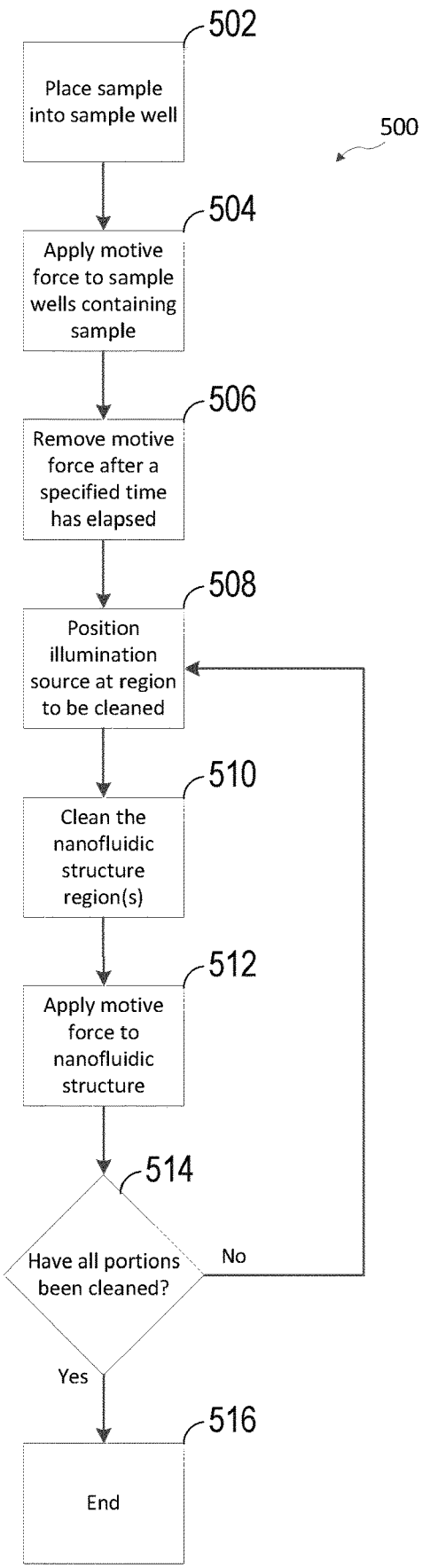
FIG. 5 is a flow diagram of a process for cleaning a nanofluidic or microfluidic structure after being used to linearize biopolymer molecules.

FIG. 4 depicts one exemplary embodiment of a control system 400 for a biopolymer analysis system that may automatically or manually perform the method disclosed in FIG. 5. A control system 400 includes a controller 462 and a memory 464. The controller 462 is in communication with the memory 464. The controller may comprise a processor and an internal memory or cache. The memory 464 may contain computer-readable instructions for operating the controller 462 and/or the control system 400.

The controller 462 is also advantageously in communication with the illumination source(s) 460, one or more x, x-y, or x-y-z translation motors 492, and a motive force generator 494. The controller 462 is configured to power on or off the illumination source(s) 460 and may also control the intensity of the illumination source(s) 460 and/or the duration of illumination. In some embodiments, the illumination source(s) 460 may provide control of the wavelength of light to be emitted, or may be selected to have strong or peak emissions at a desired wavelength, such as a wavelength at which a biopolymer or label effectively absorbs photons in a manner sufficient to effect cleavage. The controller 462 may be configured to control the direction, focus, or wavelength of the illumination beam by controlling the illumination optics 470. The illumination source(s) 460 and the illumination optics 470, individually or in combination, may advantageously comprise, for example, a laser light energy source or an LED light energy source, or any other source of photons effective to photocleave the biopolymer in question.

The controller 462 is configured to send control signals to one or more x, x-y, x-y-z translation motors 492, such as are described herein. For example, the controller 462 may be configured to control operation of the x, x-y, or x-y-z translation motor 492 in order to move the nanofluidic or microfluidic structures discussed above to bring portions of the nanofluidic or microfluidic structure into range/view of the illumination optics 470 and illumination source(s) 460, as needed or desired. Alternatively, the x, x-y, or x-y-z translation motor 492 may move the illumination optics 470 and/or the illumination source(s) 460 to direct light energy to a specific region or portion of the nanofluidic or microfluidic structure that is clogged or is otherwise is desired to be cleaned. It should be noted that prophylactic or preventative cleaning is also contemplated, so that accumulated biopolymer can be removed even if no decrease or only minor decrease in performance has occurred. In some embodiments, the photocleaving cleaning method described herein may be used prophylactically to prevent clogging, or may be used in conjunction with other prophylactic cleaning methods. In some embodiments, the translation motor 492 may be replaced with the positioning system described above. The controller 462 can be configured to operate or supply control signals to the motive force generator 494. The motive force generator may comprise electrodes, pressure generating elements, or other components configured to generate a motive force as described herein. The motive force, as described above, may be configured to move the biopolymer molecules through the fluidic device and into the detection region.

In some embodiments, the controller 462 operates by automatically controlling and coordinating the timing of operating the illumination source(s) 460, the motive force generator 494, the illumination optics 470, and the other portions of the control system 400. For example, in some embodiments, the controller 462 can supply a signal to the motive force generator 494 to induce movement of biopolymers or macromolecules in a fluidic system. After an amount of time has passed, the controller 462 may remove the signal, or may provide an interrupt signal to stop application of the motive force from the motive force generator 494. After the motive force is removed, the controller 462 may provide a signal to the illumination source(s) 460 to illuminate a portion of the nanofluidic or microfluidic structure which may be clogged with biopolymers or macromolecules or may otherwise be desired to be cleaned. In some embodiments, the controller 462 may determine that the nanofluidic or microfluidic structure of the biopolymer analysis system needs to be cleaned. As discussed above, this determination may be based on the flow rate of the biopolymers through the nanofluidic or microfluidic structure. In other embodiments, the controller 462 may clean the nanofluidic or microfluidic structure after every sample of biopolymers is analyzed by the biopolymer analysis system. Note that while automated systems are disclosed, a manual or partially manual system may also be used, if desired. For example, a cleaning cycle could be initiated when a user hits a button, makes a menu selection, manually translates the x, x-y, or x-y-z motor to irradiate specific portions of the fluidic device, or otherwise initiates a cleaning cycle. This could occur whenever a user desires, or can occur, for example, in response to a notification provided by the controller to a user requesting input if the user agrees to initiate cleaning.

Cleaning the nanofluidic or microfluidic structure may comprise dosing the region or portion of the nanofluidic or microfluidic structure to be cleared. In one exemplary embodiment, such as when biopolymer molecules such as DNA is labeled with a dye or other molecule that absorbs at 473 nm, the laser dosing process may involve dosing each biopolymer molecule with between 1 and 100 MJ/m^2 of 473 nm laser energy density per cycle depending on the biopolymer molecules that are being analyzed with the biopolymer analysis system. For example, in one embodiment, the most common energy density per cycle may be 15 MJ/m^2 of 473 nm laser. Additionally, in other embodiments, different wavelengths of laser may be used, such as when DNA is labeled with a different dye or other absorber. A designer can readily determine an appropriate energy density per cycle that is effective to photocleave the biopolymer molecules. In this manner, biopolymer molecules that previously clogged a portion of the nanofluidic or microfluidic structure or otherwise clogged, reduced, or inhibited the flow of biopolymer molecules through the fluidic structure may be cleaved or "chopped" into smaller pieces that can pass from the regions in which such biopolymer molecules have accumulated.

The controller 462 may control the dosing energy of the laser dosing process described above by turning on and off the illumination source(s) 460 and directing the illumination to the appropriate location using the illumination optics 470. The controller 462 may determine what energy density should be used based on the biopolymer molecule in each sample and based on the light energy source being used to photocleave the biopolymer molecules. For example, as mentioned above, DNA molecules being photocleaved by a 473 nm laser may require 15 MJ/m^2 to photocleave when the DNA molecules have been stained with a YoYo-1 fluorescent label. Alternatively, photocleaving DNA molecules using UV light may not require staining but may require more energy during dosing than that of the 473 nm laser. The controller 462 may thus determine the amount of time to expose the portion of the nanofluidic or microfluidic structure being cleaned to the illumination source(s) 460 and the illumination optics 470 and may provide the desired energy level to the device. Control of the energy level may be achieved by any appropriate means, such as by pulse width modulation, control of energy input into the illumination source 460, filtering, or changing the illumination time.

During, or after at least a portion of the fluidic system is illuminated, the controller 462 may signal the motive force generator 494 to activate. Activating the motive force generator 494 after the photocleaving process may flush out the photocleaved fragments of the biopolymer. After the motive force generator 494 is deactivated, the controller 462 may signal the x, x-y, or x-y-z translation motor 492 to move the nanofluidic or microfluidic structure a specified amount to position the next portion to be cleaned within range of the illumination source(s) 460 and illumination optics 470, or may move the illumination source(s) 460 and illumination optics 470 to the appropriate location to clean the next portion of the nanofluidic or microfluidic structure that needs to be cleaned. After the nanofluidic or microfluidic structure or the illumination source(s) 460 and optics 470 have been moved, the controller 462 may re-energize the illumination source(s) 460 and optics 470 to properly dose the new portion of the nanofluidic or microfluidic structure and flush the chopped portions of biopolymer molecules to clear the next region of the nanofluidic or microfluidic structure. This process may repeat as many times as needed to fully clean and clear all clogged portions of the nanofluidic or microfluidic structure, or as desired. Alternatively some or all of the areas to be cleaned may be scanned with laser or other optical energy one or more times in a repetitive manner until sufficient cleaving energy has been administered. This process will be described in more detail with respect to FIG. 5.

FIG. 5 is a flow diagram of an exemplary process for cleaning a nanofluidic or microfluidic structure after being used to linearize biopolymer molecules. A process 500 for cleaning a nanofluidic or microfluidic structure may begin at block 502, wherein a sample containing an optionally marked, tagged, or stained biopolymer, such as DNA is added to a first reservoir or sample well. In some embodiments, a buffer solution or identical or other liquid or fluid may be added to a second reservoir or sample well, in order to facilitate the electrophoresis of the biopolymer or macromolecule. Following addition of the sample, the biopolymer analysis system may form a seal around the reservoir or the nanofluidic or microfluidic structure to prevent evaporation of the sample. In some embodiments, the biopolymer analysis system may include negative and positive electrodes. The negative and positive electrodes, or portions thereof, may be brought into contact with the sample in the first reservoir or sample well and the buffer solution or liquid in the second reservoir or sample well, respectively, to provide an electrostatic force to move the biopolymer molecules. In other embodiments, the motive force may comprise the pressure force generated by the pressure generation element as described above, which is brought into position after the sample is placed in the reservoir or sample well.

The process moves to block 504, wherein the motive force is applied to the reservoirs or sample wells. As described above, in some embodiments, this is accomplished by applying an electric field to the sample wells by using, for example, the negative and positive electrodes, and/or the electrode portions of the substrate. In some embodiments, this is accomplished by applying a pressure gradient sufficient to drive molecules from the first reservoir to the second reservoir through the microchannels or nanochannels.

The process 500 moves to block 506, wherein the motive force is removed after a predetermined amount of time. In some embodiments, block 506 may comprise removing the motive force when the flow through the nanofluidic or microfluidic structure drops below a threshold value, indicating the flow through the nanochannels is complete. Alternatively, the block 506 may be timed to allow biopolymers in the nanochannels to move out of the nanochannels and other biopolymers to move into the nanochannels for imaging or other analysis. Upon removal of the motive force in block 506, the movement, driving, or migration of molecules through the nanofluidic or microfluidic structure, and, specifically, the nanochannels stops, and the molecules maintain their current positions, either within the nanochannels or in the second reservoir or sample well. The predetermined amount of time may be determined based on the biopolymer or macromolecule of interest. In some embodiments, the predetermined amount of time may be determined based on the quantity of biopolymer molecules being linearized and transported by the system. The time the motive force is applied may be 1 microsecond, 5 microseconds, 10 microseconds, 20 microseconds, 50 microseconds, 0.1 seconds, 0.5 seconds, 1 second, 2 seconds, 3 seconds, 4 seconds, 5 seconds, 10 seconds, 15 seconds, 20 seconds, 25 seconds, 30 seconds, 45 seconds, 60 seconds, 90 seconds, 120 seconds, 5 minutes, 10 minutes, 15 minutes, 20 minutes, 30 minutes, or more, or any amount of time therebetween.

The process 500 moves to block 508 wherein either the illumination optics or the nanofluidic or microfluidic structure is moved so as to direct illumination for cleaning by a light energy source to be directed onto a desired region of the fluidic structure. For example, if the fluidic structure is to be moved, an assembly or a platform on which the nanofluidic or microfluidic structure is attached may be moved to bring the nanofluidic or microfluidic structure into position for cleaning. In some embodiments, for example, a first portion to be cleaned may include the point where the nanochannels meet the sample well, while a second portion may include the nanochannels themselves. In some embodiments, the second portion cleaned may include an array of pillars or a subset of nanochannels, other than those previously cleaned. A person of skill in the art will understand that the second portion of the nanofluidic or microfluidic structure cleaned may vary without departing from the scope of this application.

Alternatively, at block 508, the illumination optics may be moved so as to position the illumination optics to clean a portion of the nanofluidic or microfluidic structure or biopolymer analysis system. In some of embodiments, the illumination optics may be moved to clean a portion of the nanofluidic or microfluidic structure or biopolymer analysis system that is immovable. Similarly as described above, the illumination optics may be operated to direct the illumination beam at a different portion of the nanofluidic or microfluidic structure or the biopolymer analysis system, or to scan an area, which can then be cleaned using the illumination beam. In some embodiments, for example, a first portion of the biopolymer analysis system to be cleaned may include nanofluidic or microfluidic structure comprising the nanochannels or an area adjacent to or upstream from an entrance into the nanochannels. Furthermore, a person of skill in the art will understand that any portion of a fluidic system using biopolymers that can be exposed to the illumination beam may be cleaned using a similar process, adapted as necessary to the particular system in question. Alternatively, an appropriate source of photon energy, such as a UV LED or visible light LED, or an array or arrangement of such LEDs, may be permanently positioned to direct photo-cleavage light energy when actuated onto appropriate portions of a fluidic device.

At block 510, a portion of the nanofluidic or microfluidic structure (or biopolymer fluidic system) is cleaned. This block may comprise exposing a portion of the fluidic structure to an illumination beam such that any biopolymer molecules that are remaining in that portion are dosed with energy from the illumination beam that may react with the biopolymer molecules and photocleave the biopolymer molecules that are appropriately dosed such that the biopolymer is chopped into smaller pieces. As discussed above, the dosing requirements may vary according to at least one of the biopolymer molecule, the staining or labeling element used, or the illumination source being used. In some embodiments, block 510 may be directed to specific locations that are determined to need to be cleaned. In some embodiments, block 510 may be directed to all location of the chip. After photocleaving the selected region of the nanofluidic or microfluidic structure, the process proceeds to block 512.

Block 512 may represent an optional dedicated cleaning block that may be inserted after block 510, where the nanofluidic or microfluidic structure region(s) or the portion of the biopolymer analysis system was previously cleaned. The optional block 512 may provide for the application of a dedicated motive force to the nanofluidic or microfluidic structure or the portion of the biopolymer analysis system that has been cleaned by a previous step. The dedicated motive force may be dedicated to flushing out the chopped pieces of the biopolymer molecules and leaving the area clear of elements that may inhibit the flow of biopolymers through the system. In some embodiments, the processes of optional block 512 may be performed after the optional decision block 514. In some embodiments, a non-dedicated motive force, such as a motive force used to load the DNA into the chip after a photocleavage step (e.g., the motive force of Block 504) may be used to clear the chopped pieces of the biopolymer molecules concurrently with the loading of the next DNA sample.

The process 500 moves to an optional decision state 514 wherein it is determined if each portion of the nanofluidic or microfluidic structure or biopolymer analysis system that needed to be cleaned or was scheduled to be cleaned has been cleaned. The portion to be cleaned can include a specific nanochannel or the full array of nanochannels, or the pillar array (if one exists), or any desired portion of a nanochannel or fluidic device. If the nanofluidic or microfluidic structure or biopolymer analysis system has not been fully cleaned, the process returns to step 508, wherein the cleaning of portions of the fluidic structure or biopolymer analysis system continues.

The process 500 described above may provide an increase in biopolymer molecule loading or throughput through the fluidic system. This increase in loading and throughput may be accomplished without observed side effects, such as decreased DNA size, photobleached labels or other related metrics. Additionally, in systems where the cleaning method may be utilized after every loading instance, the biopolymer analysis system may be more aggressively loaded than in a biopolymer analysis system that is not cleaned, leading to higher throughput.

A person of skill in the art will understand that the steps of process 500 need not be performed in the order specified, nor must all steps be performed. Furthermore, a person of skill in the art will understand that the processes may be performed in parallel, and no steps in one process necessarily preclude the performance of steps in another process. In some embodiments, the processes occur in an overlapping fashion, with steps from one process giving rise to or, initiating steps from another process, or steps from one process being triggered by steps from another process. The process may be fully automatic, may be partially automated while requiring one or more user inputs, or may be manually implemented.

Figure 6:
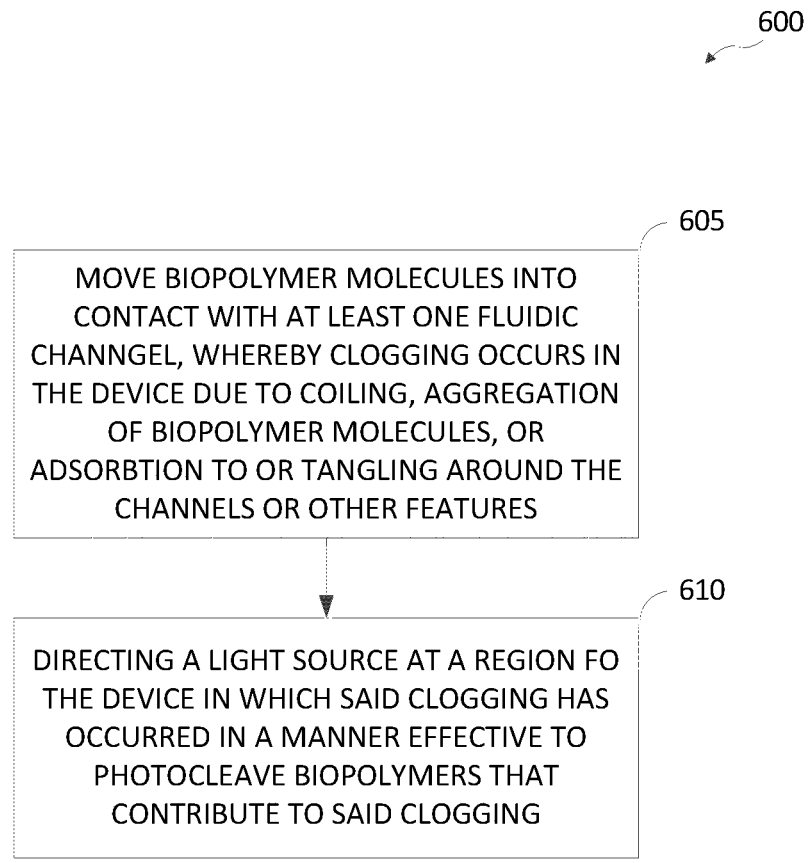
FIG. 6 is a flowchart of one exemplary method of enhancing fluid flow. In some aspects, the process 600 may be performed by the biopolymer molecule analysis system 400.

FIG. 6 is a flowchart of one exemplary method of enhancing fluid flow. In some aspects, the process 600 may be performed by the control system 400. In some aspects, the process 600 may be performed by a standalone photocleaving system (not shown). Process 600 may demonstrate the process of cleaning a nanofluidic or microfluidic structure after being used to linearize biopolymer molecules, for example the process 500 shown in FIG. 5.

At block 605, biopolymer molecules may be moved into contact with at least one fluidic channel in or on a device, whereby clogging occurs in the device due to coiling or aggregation of the biopolymer molecules or adsorbtion to or tangling around the channels or other nano- or micro-patterned features inside the channel or fluidic device. In some aspects, the biopolymer molecules may be moved using a motive force to flush photocleaved biopolymer molecules from the cleaned region. In some aspects, the motive force may comprise an electrostatic, a pneumatic force, a capillary force, or any combination thereof.

At block 610, the process 600 may direct a light source at a region of the device in which said clogging has occurred so as to photocleave any biopolymer molecules that contribute to said clogging and facilitate removal or reduction of said clogging. In some embodiments, the light source may emit a light having a wavelength of 473 nm or 488 nm. In some aspects, the process 600 may further include labeling the biopolymer molecules with an indicator to facilitate photocleaving of the biopolymer molecules when exposed to the light source. In some aspects, the block 610 or another block of process 600 (not shown in this figure) may configure the light source to generate light that matches the indicator or photon absorber used to label the biopolymer molecules to maximize the photocleaving capabilities of the process. Generating light that matches the indicator or photon absorber may comprise determining what characteristics of the light (i.e., wavelength, intensity, etc.) would maximize photocleaving of the biopolymer molecules labeled with particular indicators or photon absorbers. Each indicator or photon absorber may have a different light (i.e., light with a different wavelength, intensity, etc.) that maximizes photocleavage of the biopolymer molecules to which the indicator or photon absorber is applied. In some aspects, the process 600 may further include detecting a clogged or reduced flow condition prior to or concurrent with or after the block 610. In some aspects, the process 600 may be implemented automatically by system 400 at one of a predetermined time or predetermined transport threshold. Any of the blocks described above in relation to process 600 may be performed by one or more of the components of system 400, including the controller 462, the illumination source(s) 460 and optics 470, motive force generate 494, and x, x-y, or x-y-z translation motor 492. In some embodiments, one or more of the blocks described above may be performed by components of similar structure and function as those depicted in FIG. 4.

The technology is operational with numerous other general purpose or special purpose computing system environments or configurations. Examples of well-known computing systems, environments, and/or configurations that may be suitable for use with the invention include, but are not limited to, personal computers, server computers, hand-held or laptop devices, multiprocessor systems, processor-based systems, programmable consumer electronics, network PCs, minicomputers, controllers, microcontrollers, mainframe computers, multiple processors directly or indirectly linked, distributed computing environments that include any of the above systems or devices, and the like. Combinations of these devices can be used together.

As used herein, instructions refer to computer-implemented steps for processing information in the system. Instructions can be implemented in software, firmware or hardware and include any type of programmed step undertaken by components of the system.

As used herein, a processor may be any conventional general purpose single- or multi-chip processor such as a Pentium® processor, a Core I3, I5, or I7 processor, a 8051 processor, an AMD FX series processor, a MIPS® processor, an Atom processor, an Alpha® processor, or any other desired or suitable processor or combination of processors. In addition, the processor may be any conventional special purpose processor such as a digital signal processor a graphics processor or an embedded microcontroller. The processor typically has conventional address lines, conventional data lines, and one or more conventional control lines.

The system is comprised of various modules as discussed in detail. As can be appreciated by one of ordinary skill in the art, each of the modules comprises various sub-routines, procedures, definitional statements and macros. Each of the modules are typically separately compiled and linked into a single executable program. Therefore, the description of each of the modules is used for convenience to describe the functionality of the preferred system. Thus, the processes that are undergone by each of the modules may be arbitrarily redistributed to one of the other modules, combined together in a single module, or made available in, for example, a shareable dynamic link library.

The system may be used in connection with various operating systems such as Linux®, UNIX® or Microsoft Windows®.

The system may be written in any conventional programming language such as C, C++, C#, BASIC, Pascal, or Java, and run under a conventional operating system. C, C++, BASIC, Pascal, Java, and FORTRAN are industry standard programming languages for which many commercial compilers can be used to create executable code. The system may also be written using interpreted languages such as Perl, Python or Ruby.

Those of skill will further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

One of skill will further appreciate that the methods and apparatus described herein may be applied to any fluidic system making use of biopolymer molecules in situations where clogs may develop.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

In one or more example embodiments, the functions and methods described may be implemented in hardware, software, or firmware executed on a processor, or any combination thereof. If implemented in software, the functions may be stored on or transmitted over as one or more instructions or code on a computer-readable medium. Computer-readable media include both computer storage media and communication media including any medium that facilitates transfer of a computer program from one place to another. A storage medium may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

The foregoing description details certain embodiments of the systems, devices, and methods disclosed herein. It will be appreciated, however, that no matter how detailed the foregoing appears in text, the systems, devices, and methods can be practiced in many ways. As is also stated above, it should be noted that the use of particular terminology when describing certain features or aspects of the invention should not be taken to imply that the terminology is being redefined herein to be restricted to including any specific characteristics of the features or aspects of the technology with which that terminology is associated.

It will be appreciated by those skilled in the art that various modifications and changes may be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting.

What is claimed is:

1. A method for enhancing fluid flow, the method comprising:

moving biopolymer molecules into contact with at least one fluidic channel in or on a device, whereby clogging occurs in the device due to coiling or aggregation of the biopolymer molecules, or adsorption or tangling of the biopolymer molecules around the channels or any other nano- or micro- features inside the channel or fluidic device;

detecting a clogged or reduced flow condition, wherein the detection comprises identifying that a transport of the biopolymer molecules through the device falls below a threshold transport value;

directing a light source at a region of the device in which said clogging has occurred in a manner effective to photocleave at least one of the biopolymer molecules that contribute to said clogging, thereby facilitating removal or reduction of said clogging;

after directing the light source to the region, applying a motive force to fluid in the region in a manner effective to flush the photocleaved biopolymer molecules creating said clog from the region of the device in which said clogging has occurred; and applying a motive force to flow additional biopolymer molecules through the device for characterization, wherein flushing the photocleaved biopolymer molecules and flowing additional biopolymer molecules are concurrent.

2. The method of claim 1, wherein the motive force comprises an electrostatic force, a pneumatic force, a capillary force, or any combination thereof.

3. The method of claim 1, wherein the biopolymer molecules comprise DNA or RNA.

4. The method of claim 1, further comprising labeling the biopolymer molecules with an indicator to facilitate photocleavage of the biopolymer molecules when exposed to the light source, wherein the light source is configured to generate a light matched with the indicator to enhance photocleaving capabilities.

5. The method of claim 4, wherein the indicator used to label the biopolymer molecules comprises one or more of YOYO-1, YOYO-3, TOTO, methylene blue, Cu, Rh, compounds useful for photodynamic therapy, and other photon absorbers capable of facilitating cleavage of the biopolymer upon irradiation with photons.

6. The method of claim 5, wherein the indicator is YOYO-1 and the light source has a wavelength of one of about 473 nm or about 488 nm.

7. The method of claim 1, wherein the detection comprises direct imaging of at least one fluidic channel in or on the device to indicate clogging.

8. The method of claim 1, wherein a cleaning of the region of the device in which the clogging has occurred is implemented in an automatic fashion at one of a predetermined time or a predetermined transport threshold.

9. The method of claim 1, further comprising positioning the light source in a manner effective to minimize exposure of the device other than the region of the device in which said clogging has occurred to the light source.

10. An apparatus for enhancing fluid flow, the apparatus comprising:
- a light source configured to generate a light beam configured to photocleave biopolymer molecules clogged within a channel, wherein the biopolymer molecules comprise DNA or RNA;
- a pillar region comprising a plurality of pillars configured to untangle, uncoil, and/or straighten biopolymer molecules;
- a controller configured to:
  - control a movement of the biopolymer molecules into contact with at least one fluidic channel in or on a device, whereby clogging occurs in the device due to coiling or aggregation of the biopolymer molecules, or adsorption to or tangling of the biopolymer molecules around the channels or other nano- or micropatterned features inside the channel or fluidic device;
  - determine a region of the device in which the clogging has occurred;
  - direct the light source at the region of the device in which the clogging has occurred;
  - activate the light source to generate the light beam for an amount of time to facilitate a photocleaving of the biopolymer molecules causing said clogging; and
  - after activating the light source, apply a motive force to fluid in the location in a manner effective to flush the photocleaved biopolymer molecules from the region of the device comprising said clogging, thereby enhancing fluid flow; and
- a detector configured to detect a clog or reduced flow condition through the at least one fluidic channel in or on the device, wherein the detector is further configured to identify that a transport of biopolymer molecules through the at least one fluidic channel in or on the device falls below a threshold transport value.

11. The apparatus of claim 10, further comprising a motive force generator configured to generate the motive force, wherein the controller is configured to control a movement of the biopolymer molecules via the generated motive force.

12. The apparatus of claim 11, wherein the motive force comprises an electrostatic force, a pneumatic force, a capillary force, or any combination thereof.

13. The apparatus of claim 10, wherein the motive force generator is configured to generate one of an electrostatic force or a pneumatic force.

14. The apparatus of claim 10, wherein the light beam generated by the light source has a wavelength of one of about 473 nm or about 488 nm.

15. An apparatus for characterizing a biopolymer molecule, the apparatus comprising:
- a fluidic device comprising a detection region comprising at least one channel, and further comprising the biopolymer molecule;
- a pillar region comprising a plurality of pillars configured to untangle, uncoil, and/or straighten biopolymer molecules;
- a motive force generator to move biopolymer molecules into the detection region, wherein the movement of the biopolymer molecules causes at least one of the biopolymer molecules to at least one of coil, aggregate, adsorb to, or tangle around at least a portion of the fluidic device, causing a clog which hampers further flow of new biopolymer molecules to the detection region;
- a detection system for determining a characteristic of the biopolymer molecules in the detection region;
- a light source set to deliver a light comprising a configuration for photocleaving the biopolymer molecules forming the clog;
- a light delivery system to deliver the light to any region of the fluidic device;
- a detector configured to detect a clog or reduced flow condition through the at least one fluidic channel in or on the device, wherein the detector is further configured to identify that a transport of biopolymer molecules through the at least one fluidic channel in or on the device falls below a threshold transport value;
- a positioning system to target the detection system to the detection region for characterization of the biopolymer molecules, and to target the light comprising the photocleaving configuration to a region of the device where the clog has formed; and
- a controller configured to:
  - activate the motive force generator to move the biopolymer molecules into the detection region;
  - direct the detection system to the detection region;
  - activate the detection system to determine the characteristics of the biopolymer molecules;

direct the light source configured for photocleaving biopolymer molecules to the region where the clog has formed;

activate the light source to generate a light for photocleaving biopolymer molecules forming the clog; and activate the motive force generator after activating the light source to flush out the photocleaved biopolymer molecules, wherein additional new biopolymer molecules flow into the detection region for characterization after the motive force generator flushes out the photocleaved biopolymer molecules.

16. The apparatus of claim 15, further comprising a plurality of relaxation channels having a wider dimension at an end adjacent to the pillar region and a narrow dimension at the other end.

\* \* \* \* \*